(12) United States Patent
Kitada (10) Patent No.: US 12,085,551 B2
(45) Date of Patent: Sep. 10, 2024

(54) WATER QUALITY ANALYZER

(71) Applicant: SHIMADZU CORPORATION, Kyoto (JP)

(72) Inventor: Yoshio Kitada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 440 days.

(21) Appl. No.: 17/420,239

(22) PCT Filed: Oct. 3, 2019

(86) PCT No.: PCT/JP2019/039119
§ 371 (c)(1),
(2) Date: Jul. 1, 2021

(87) PCT Pub. No.: WO2020/144902
PCT Pub. Date: Jul. 16, 2020

(65) Prior Publication Data
US 2022/0065839 A1 Mar. 3, 2022

(30) Foreign Application Priority Data

Jan. 11, 2019 (JP) .............................. 2019-003149

(51) Int. Cl.
*G01N 33/18* (2006.01)
*G01N 1/14* (2006.01)
*G01N 21/33* (2006.01)

(52) U.S. Cl.
CPC .............. *G01N 33/18* (2013.01); *G01N 1/14* (2013.01); *G01N 21/33* (2013.01); *G01N 2201/06113* (2013.01)

(58) Field of Classification Search
None
See application file for complete search history.

(56) References Cited

U.S. PATENT DOCUMENTS 4,517,302 A * 5/1985 Saros .................... G01N 35/08
73/864.22
5,013,488 A * 5/1991 Abadi .................... G01N 9/14
137/91

(Continued)

FOREIGN PATENT DOCUMENTS

JP      51-014399 B1    5/1976
JP      2004-069448 A   3/2004

(Continued)

OTHER PUBLICATIONS

Office Action dated Jul. 26, 2022 from the Japanese Patent Office in JP Application No. 2020-565579.

(Continued)

*Primary Examiner* — Marcus H Taningco
(74) *Attorney, Agent, or Firm* — Sughrue Mion, PLLC (57) ABSTRACT

A water quality analyzer includes: a sample reservoir (20) including a first storage container (22) configured to temporarily store sample water supplied from a sample water source, and a discharge mechanism (24) configured to discharge the sample water to an outside of the first storage container (22); at least one second storage container (32) provided as a container different from the first storage container (22) for storing the sample water; a measurement device (10) including a measurement cell (12) for accommodating sample water, the measurement device (12) being configured to obtain a measured value of a physical quantity related to the sample water accommodated in the measurement cell (12); a pump (2) configured to suction and discharge a liquid, wherein the pump (2) is fluidly connected to any one of the first storage container (22), the second storage container (32), and the measurement cell (12) selectively; a switching device (4;6) configured to switch fluidly connection of the pump (2) with the first storage container (22), the second storage container (22) and the measurement cell (12); a determination part (40) configured to determine whether the measured value is normal or abnormal by (Continued)

comparing the measured value with a preset threshold; a measurement controller (38) configured to transfer the sample water stored in the first storage container (22) to the measurement cell (12) using the pump (2) by controlling an operation of the pump (2) and an operation of the switching device (4;6); a first storage controller (42) configured to control an operation of the sample reservoir (20), wherein the first storage controller (42) is configured, after a portion of the sample water stored in the first storage container (22) is supplied to the measurement cell (12) by the pump (2), to make the sample water in the first storage container (22) to remain in the first storage container (22) until the determination part determines the measured value of the sample water which has supplied to the measurement cell (12), and wherein the first storage controller (42) is configured to discharge the sample water remaining in the first storage container (22) to the outside of the first storage container (22) in a case where the determination part (40) determines that the measured value obtained by the measurement device (10) is normal; and a second storage controller (44) configured to transfer the sample water remaining in the first storage container (22) to the second storage container (32) in a case where the determination part (40) determines that the measured value obtained by the measurement device (10) is abnormal.

7 Claims, 2 Drawing Sheets

(56) References Cited

U.S. PATENT DOCUMENTS

| | | | | |
|---|---|---|---|---|
| 7,311,818 | B1* | 12/2007 | Gurfinkel | B01D 21/30 |
| | | | | 210/103 |
| 7,504,028 | B1* | 3/2009 | Gurfinkel | E02B 15/104 |
| | | | | 210/170.11 |
| 10,627,384 | B1* | 4/2020 | Kitada | G01N 21/59 |
| 2007/0254374 | A1* | 11/2007 | Iharada | G01N 33/1846 |
| | | | | 436/146 |
| 2011/0176976 | A1* | 7/2011 | Ebi | G01N 35/04 |
| | | | | 422/547 |
| 2017/0197845 | A1* | 7/2017 | Hashimoto | C02F 1/725 |
| 2018/0364152 | A1* | 12/2018 | Naor | G01N 21/05 |
| 2020/0096423 | A1* | 3/2020 | Komori | G01N 1/24 |

FOREIGN PATENT DOCUMENTS

| | | |
|---|---|---|
| JP | 2009-192340 A | 8/2009 |
| JP | 2016-080441 A | 5/2016 |
| JP | 2017-223583 A | 12/2017 |
| JP | 2018-059788 A | 4/2018 |

OTHER PUBLICATIONS

Extended European Search Report dated Aug. 2, 2022 from the European Patent Office in EP Application No. 19909611.6.

International Search Report for PCT/JP2019/039119 dated Dec. 10, 2019.

Written Opinion for PCT/JP2019/039119 dated Dec. 10, 2019.

Communication dated Mar. 29, 2023 from the European Patent Office in Application No. 19909611.6.

Office Action issued Dec. 9, 2022 in Chinese Application No. 201980088579.2.

Chinese Office Action dated Aug. 17, 2023 in Chinese Application No. 201980088579.2.

* cited by examiner

WATER QUALITY ANALYZER

TECHNICAL FIELD

The present invention relates to a water quality analyzer.

BACKGROUND ART

As a water quality analyzer such as a total organic carbon measurement device (TOC meter) or a total phosphorus measurement device (TP meter), there has been generally used a water quality analyzer which performs an oxidation reaction treatment of sample water by adding an oxidizing agent such as potassium persulfate to the sample water in a reactor and, thereafter, transfers the sample water to a measurement cell, and measures absorbance or the like (see, for example, Patent Document 1).

PRIOR ART DOCUMENT

Patent Document

Patent Document 1: Japanese Patent Laid-open Publication No. 2018 059788

SUMMARY OF THE INVENTION

Problems to be Solved by the Invention

Amongst water quality analyzers, there has been known a device which is referred to as an online water quality analyzer. The online water quality analyzer is a device that periodically collects wastewater continuously flowing out from a factory or the like as sample water, and continuously and automatically performs the measurement of the sample water.

In the online water quality analyzer described above, a predetermined amount of sample water is collected at a fixed time interval so as to measure the absorbance or the like of the sample water. However, remaining sample water other than the predetermined amount of sample water to be subjected to the measurement is discharged. Accordingly, the same sample does not remain in the device at a point of time that the measurement is completed. Therefore, even when a measured value exhibits an abnormal value, the sample water which exhibits such a measured value does not remain in the device. As a result, there has been no way of verifying whether the indication of the abnormal measured value is attributed to the sample water or to the occurrence of an abnormality in the device.

In view of the above-mentioned circumstances, it is an object of the present invention to provide a water quality analyzer which can verify whether or not the occurrence of an abnormality in a measured value of sample water is attributed to the sample water when such an abnormality occurs in the measured value.

Solutions to the Problems

A water quality analyzer according to the present invention includes: a sample reservoir including a first storage container configured to temporarily store sample water supplied from a sample water source, and a discharge mechanism configured to discharge the sample water to an outside of the first storage container; at least one second storage container provided as a container different from the first storage container for storing the sample water; a measurement device including a measurement cell for accommodating sample water, the measurement device being configured to obtain a measured value of a physical quantity related to the sample water accommodated in the measurement cell; a pump configured to suction and discharge a liquid, wherein the pump is fluidly connected to any one of the first storage container, the second storage container, and the measurement cell selectively; a switching device configured to switch fluidly connection of the pump with the first storage container, the second storage container and the measurement cell; a determination part configured to determine whether the measured value is normal or abnormal by comparing the measured value with a preset threshold; a measurement controller configured to transfer the sample water stored in the first storage container to the measurement cell using the pump and to perform measurement of the sample water by controlling an operation of the pump and an operation of the switching device; a first storage controller configured to control an operation of the sample reservoir, wherein the first storage controller is configured, after a portion of the sample water stored in the first storage container is supplied to the measurement cell by the pump, to make the sample water stored in the first storage container to remain in the first storage container until the determination part determines the measured value of the sample water which has supplied to the measurement cell, and wherein the first storage controller is configured to discharge the sample water remaining in the first storage container to the outside of the first storage container in a case where the determination part determines that the measured value obtained by the measurement device is normal; and a second storage controller configured to transfer the sample water remaining in the first storage container to the second storage container in a case where the determination part determines that the measured value obtained by the measurement device is abnormal.

Effects of the Invention

The water quality analyzer according to the present invention includes: the first storage container for temporarily storing sample water supplied from the sample water source, and the second storage container provided as a storage container different from the first storage container for storing the sample water. The water quality analyzer is configured in such a way that the sample water is made to remain in the first storage container until determination is made whether the measured value of the sample water is normal or abnormal, and the sample water remaining in the first storage container is transferred to the empty second storage container in a case where the determination part determines that the measured value is abnormal. With such a configuration, since the sample water of which the measured value is determined to be abnormal is stored in the second storage container and remains in the device. Accordingly, it is possible to verify whether or not an abnormality of the measured value is attributed to the sample water when there is an abnormality in the measured value.

EMBODIMENT OF THE INVENTION

Hereinafter, an embodiment of a water quality analyzer according to the present invention will be described with reference to the drawings.

Figure 1:
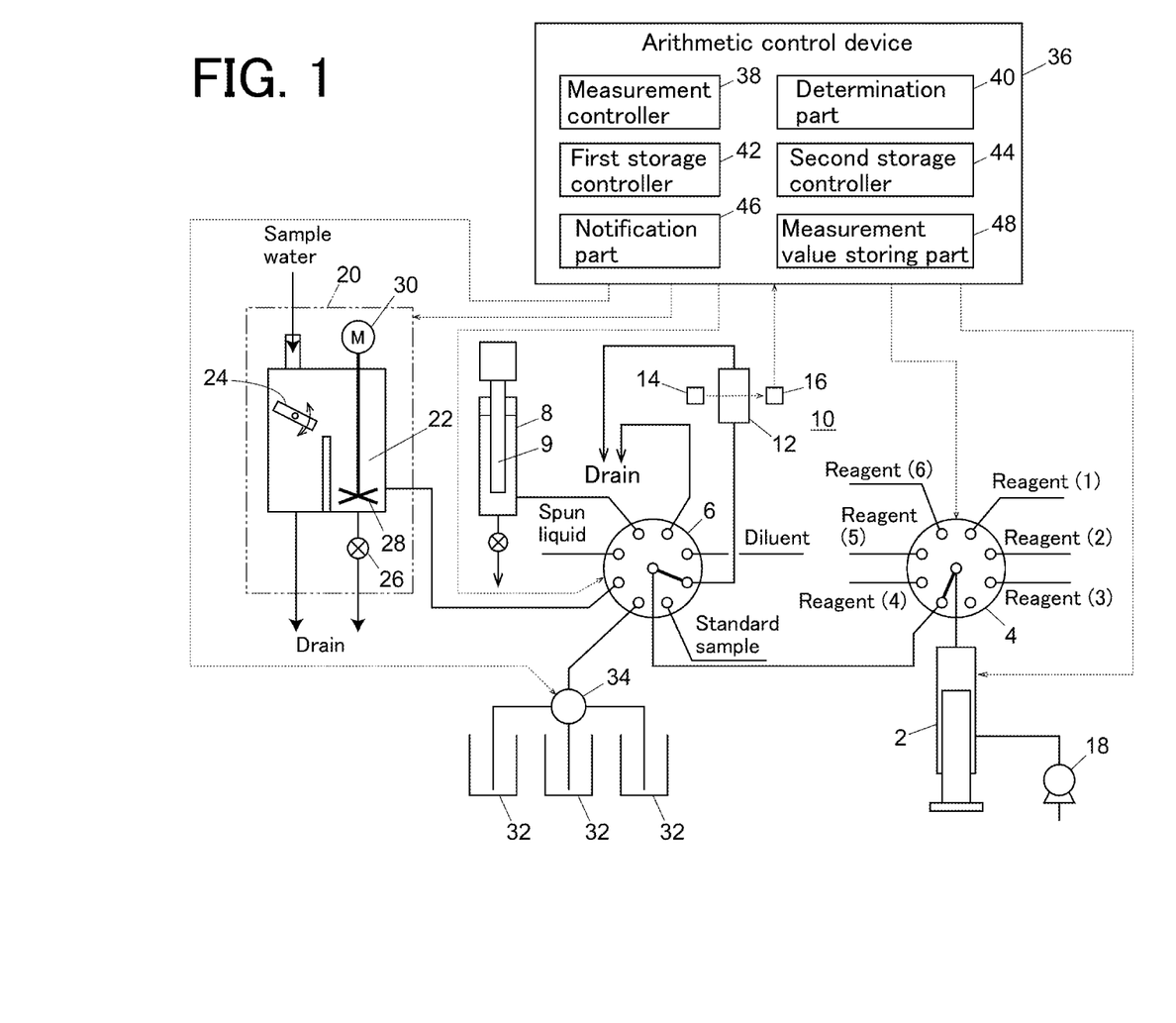
FIG. 1 is a schematic configuration view illustrating an embodiment of a water quality analyzer.

As shown in FIG. 1, the water quality analyzer of this embodiment mainly includes a syringe pump 2 (pump), two multi-port valves 4 and 6, a reactor 8, a measurement device 10, a sample reservoir 20, and an arithmetic control device 36.

The syringe pump 2 suctions and discharges a liquid. A suction/discharge port of the syringe pump 2 is connected to a center port of the multi-port valve 4. A pump 18 for stirring is connected to the cylinder of the syringe pump 2 through a flow path, and a liquid can be stirred in the syringe pump 2 by air supplied by the pump 18.

The multi-port valve 4 has one center port and a plurality of select ports, and can selectively connect the center port to any one of the select ports. A suction/discharge port of the syringe pump 2 is connected to the center port of the multi-port valve 4. One select port of the multi-port valve 4 is connected to a center port of the multi-port valve 6 through a flow path. Other select ports of the multi-port valve 4 are ports to which containers for storing reagents 1 to 6 are respectively connected.

As examples of the reagents 1 to 6, a sodium hydroxide solution, a potassium persulfate solution, a hydrochloric acid solution, a sulfuric acid solution, a molybdic acid solution, and an ascorbic acid solution can be used. The arithmetic control device 36 that controls the operation of the water quality analyzer stores which select port of the multi-port valve 4 corresponds to any one of the reagents 1 to 6.

The multi-port valve 6 also has one center port and a plurality of select ports, and selectively connects the center port to any one of the select ports. One select port of the multi-port valve 6 is connected to the reactor 8 through a flow path, and one of the other select ports of the multi-port valve 6 is connected to an inlet of a measurement cell 12 of the measurement device 10 through a flow path. To the other select ports of the multi-port valve 6, besides a flow path leading to a storage container 22 (first storage container) of the sample reservoir 20 described later and flow paths leading to containers that respectively store a spun liquid, a diluent and a standard liquid, a flow path leading to a storage container 32 (second storage container) is connected.

The storage container 32 is a container for storing the sample water when a measured value exhibits an abnormal value. In this embodiment, a plurality of storage containers 32 are provided, and the storage container 32 to be used is selectively switched by a flow path selection valve 34. It is not always necessary to provide the storage containers 32 in plural, and it is sufficient that at least one storage container 32 is provided. Further, in this embodiment, the flow path leading to the storage container 32 is connected to the select port of the multi-port valve 6. However, the flow path leading to the storage container 32 may be connected to the select port of the multi-port valve 4. In short, at least one storage container 32 maybe provided so as to be connected to the suction/discharge port of the syringe pump 2 for establishing fluid communication therebetween.

The multi-port valves 4 and 6 each forma switching device for selectively switching an element to be connected with the suction/discharge port of the syringe pump 2 for establishing fluid communication therebetween. The elements to be connected with the suction/discharge port of the syringe pump 2 for establishing fluid communication therebetween by the multi-port valves 4 and 6 include: the containers that store reagents 1 to 6, a spun liquid, a diluent, and a standard liquid; the reactor 8; the measurement cell 12, the storage container 22, and the storage containers 32.

The reactor 8 is provided for performing an oxidation treatment of a sample. The reactor 8 has an inner space for storing a liquid, and a lighting portion of an ultraviolet ray lamp 9 is inserted into the inner space. The oxidation treatment of a sample is a treatment in which, by irradiating ultraviolet rays to the sample to which an oxidizing agent (for example, potassium persulfate solution) is added while supplying an oxygen gas or air under a predetermined temperature condition (for example, 95° C.), a compound to be measured in the sample is oxidatively decomposed.

The measurement device 10 includes the measurement cell 12, a light source 14, and a light detection element 16. An outlet of the measurement cell 12 leads to a drain. The light source 14 irradiates a light having a measurement wavelength (for example, 220 nm) toward the measurement cell 12. As the light source 14, for example, a laser element can be used. The light detection element 16 is provided for detecting the intensity of a light irradiated from the light source 14 and passing through the measurement cell 12. As the light detection element 16, for example, a photodiode can be used. In the measurement device 10, for example, absorbance is obtained as a measured value of a physical quantity of a sample accommodated in the measurement cell 12.

The sample reservoir 20 includes the storage container 22, a switching mechanism 24, an electromagnetic valve 26, a stirring mechanism 28, and a motor 30. Sample water is constantly supplied from a sample water source to the sample reservoir 20, and the switching mechanism 24 switches treatment of the sample water between discharging the sample water to the drain and storing the sample water in the storage container 22. The switching mechanism 24 forms a discharge mechanism for discharging (draining) sample water to the outside of the storage container 22. Normally, the switching mechanism 24 is in a state where sample water fed from the sample water source is discharged to the drain. When a timing that the measurement of sample water is to be performed arrives, in response to a command from the arithmetic control device 36, the switching mechanism 24 is switched to a state where the sample water is guided to a storage container 22 side so that the sample water is stored in the storage container 22. The electromagnetic valve 26 is disposed on a flow path leading from the storage container 22 to the drain, and is opened when sample water stored in the storage container 22 is to be discharged. The stirring mechanism 28 is disposed in the storage container 22 and is rotated by the motor 30.

When the measurement of the sample water is performed, the sample water is stored in the storage container 22 of the sample reservoir 20 and, then, the syringe pump 2 is connected to the storage container 22 for establishing fluid communication therebetween and, then, a predetermined amount of the sample water stored in the storage container 22 is collected by the syringe pump 2. The sample water collected from the storage container 22 is transferred to the reactor 8, is subjected to oxidation treatment and, then, is transferred to the measurement cell 12 where the measurement of absorbance is performed.

The arithmetic control device 36 is provided for performing an operation control and arithmetic processing of the water quality analyzer. As the arithmetic control device 36, a dedicated computer or a general-purpose personal computer on which a central processing unit (CUP) and a storage element are mounted can be used. In this embodiment, the arithmetic control device 36 includes the measurement controller 38, a determination part 40, a first storage controller 42, a second storage controller 44, a notification part 46, and a measured value storing part 48. In the arithmetic control device 36, the measurement controller 38, the determination part 40, the first storage controller 42, the second storage controller 44, and the notification part 46 are functions acquired by the execution of programs by the CPU. The measured value storing part 48 is a function realized by a partial storage area of a storage element mounted on the arithmetic control device 36.

The measurement controller 38 is configured to measure absorbance of sample water when a predetermined measurement timing arrives. Specifically, the measurement controller 38 is configured to control the operations of the syringe pump 2, the multi-port valves 4, 6, and the sample reservoir 20. In the control, in accordance with a preset measurement schedule, when a predetermined measurement timing arrives, sample water is stored in the storage container 22 of the sample reservoir 20, the sample water which is stored in the storage container 22 is collected by the syringe pump 2, oxidation treatment or the like is applied to the collected sample water in the reactor 8 and, then, the sample water is transferred to the measurement cell 12 where absorbance measurement is performed as a final step.

The determination part 40 is configured, when the measured value of the sample water is obtained by the above measurement, to compare the measured value with a preset threshold to determine whether or not the measured value is normal. The measured value to be determined may be an output signal itself of the light detection element 16 or an absorbance value calculated based on the output signal of the light detection signal element 16. In a case where a measured value is an output signal of the light detection element 16, for example, when the measured value is equal to or larger than a threshold, the measured value can be determined to be normal, and when the measured value is less than the threshold, the measured value can be determined to be abnormal. In a case where a measured value is an absorbance value, for example, when the measured value is equal to or smaller than a threshold, the measured value can be determined to be normal, and when the measured value is larger than the threshold, the measured value can be determined to be abnormal.

The first storage controller 42 is a function of controlling the operation of the sample reservoir 20 where the first storage controller 42 controls a timing of discharging sample water remaining in the storage container 22 after a predetermined amount of sample water is collected from the storage container 22 by the syringe pump 2 to the drain.

Specifically, the first storage controller 42 performs a control such that, after a predetermined amount of sample water is collected from the storage container 22 by the syringe pump 2, the remaining sample water is made to remain in the storage container 22 until the determination part 40 determines whether or not the measured value related to the sample water is normal or abnormal. When the determination part 40 determines that the measured value is normal, the first storage controller 42 opens the electromagnetic valve 26 of the sample reservoir 20 and discharges sample water in the storage container 22 to the drain. On the other hand, when the determination part 40 determines that the measured value is abnormal, the first storage controller 42 closes the electromagnetic valve 26 until an operation described later, that is, an operation of transferring sample water to the storage container 32 is completed.

The second storage controller 44 is configured to perform an operation of transferring at least a portion (for example, a total amount) of sample water remaining in the storage container 22 to the empty storage container 32 when the determination part 40 determines that the measured value related to the sample water is abnormal. Specifically, the second storage controller 44 controls the syringe pump 2 and the multi-port valves 4 and 6 so that a portion of or the whole sample water in the storage container 22 is suctioned by the syringe pump 2 when the determination part 40 determines that the measured value related to the sample water is abnormal. The second storage controller 44 further controls the syringe pump 2, the multi-port valves 4 and 6, and the flow path selection valve 34 so that sample water suctioned by the syringe pump 2 is stored in the empty storage container 32.

There maybe a case where, when sample water is transferred from the storage container 22 to the storage container 32, a component in the sample water in the storage container 22 precipitates on a bottom portion of the storage container 22 so that the concentration of the component in the sample water transferred to the storage container 32 differs from the concentration of the component of the sample water subjected to measurement. In view of the above, the second storage controller 44 maybe configured to stir the inside of the storage container 22 by the stirring mechanism 28 by controlling the motor 30 of the sample reservoir 20 before the sample water is transferred from the storage container 22 to the storage container 32.

In a case where there is no empty storage container 32, that is, in a case where the sample water is stored in all storage containers 32 when the determination part 40 determines that the measured value related to sample water is abnormal, the second storage controller 44 does not perform the above-mentioned operation of transferring the sample water. In this case, the first storage controller 42 opens the electromagnetic valve 26 and discharges sample water remaining in the storage container 22 to the drain.

The notification part 46 is configured to notify a user that sample water has been transferred from the storage container 22 to the storage container 32 when the sample water has been transferred from the storage container 22 to the storage container 32 using the function of the second storage controller 44. The notification given to the user may be displaying of a message on a display that is electrically connected to the arithmetic control device 36 or the generation of an alarm sound.

The measured value storing part 48 stores at least a measured value determined to be abnormal by the determination part 40 in association with a determination result of the measured value, and may store all measured values in association with the determination result by the determination part 40. Further, the measuring instrument storing part 48 stores the measured value determined to be abnormal by the determination part 40 in association with information related to the storage container 32 in which sample water corresponding to the measured value (that is, the sample water subjected to the measurement when the measured value is obtained) is stored (for example, the storage container number). Such information makes it easy to determine in which storage container 32 the sample water that exhibits an abnormal measured value is stored.

Although not essential, in a case where a user inputs an instruction to execute remeasurement with respect to sample water stored in the storage container 32 to the arithmetic control device 36 when the sample water is stored in the storage container 32, the measurement controller 38 may be configured to collect a predetermined amount of sample water out of the whole sample water stored in the storage container 32 by the syringe pump 2, to transfer the collected sample water to the measurement cell 12, and to perform the measurement of the collected sample water as a final step.

Figure 2:
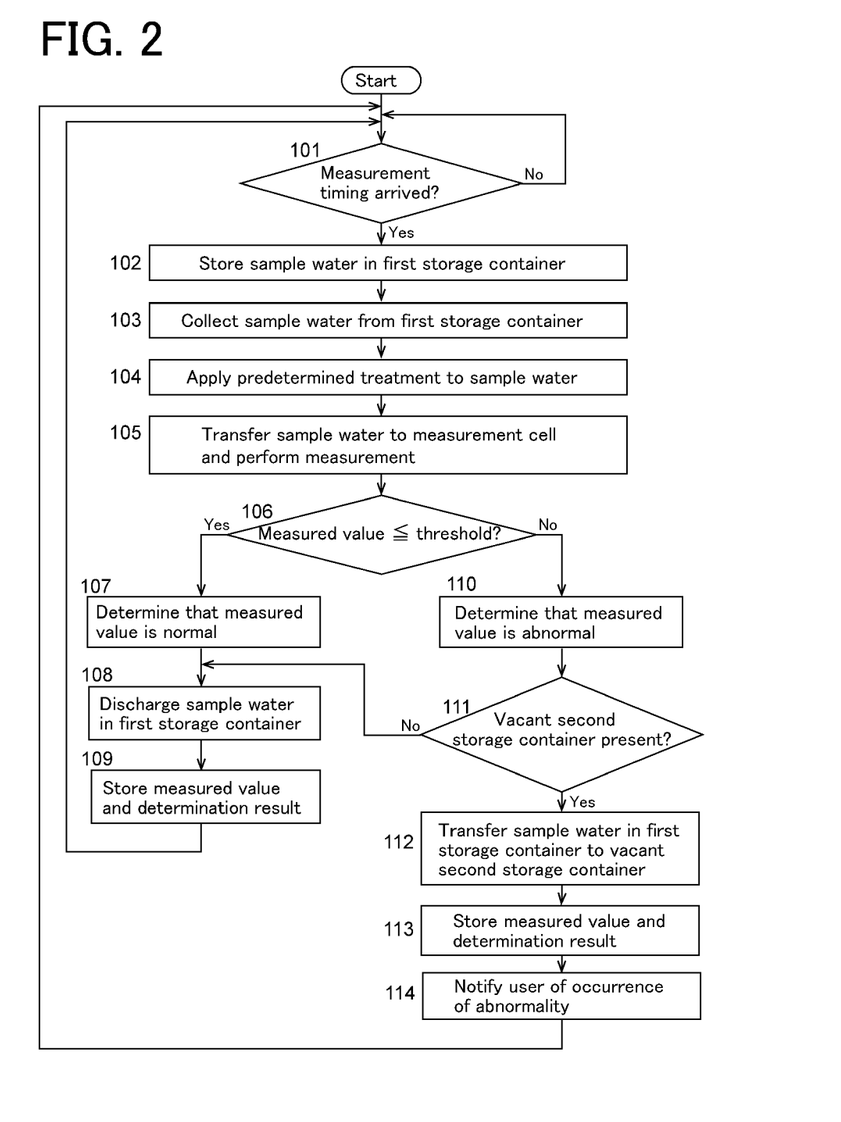
FIG. 2 is a flowchart illustrating an example of an operation of the embodiment.

Hereinafter, an example of an operation of the water quality analyzer according to this embodiment will be described with reference to the flowchart illustrated in FIG. 2 together with FIG. 1.

Sample water supplied from the sample water source to the sample reservoir 20 is discharged to the drain until a preset measurement timing arrives. When the measurement timing arrives (step 101), the measurement controller 38 switches the switching mechanism 24 into a mode where the sample water is introduced into the storage container 22 for a predetermined time so that the sample water is stored in the storage container 22 (step 102). Then, the measurement controller 38 makes the syringe pump 2 collect a predetermined amount of sample water out of the whole sample water stored in the storage container 22 (step 103), and performs a control such that the collected sample water is transferred to the reactor 8, and the reactor 8 performs oxidation treatment or the like of the sample water (step 104). After the predetermined treatment applied to the sample water is completed, the measurement controller 38 transfers the sample water to the measurement cell 12 and measures absorbance of the sample water (step 105).

When the measurement of the absorbance of the sample water is performed in the measurement device 10, the determination part 40 compares a measured value obtained in the measurement with a threshold, and determines whether the measured value is normal or abnormal (Steps 106, 107, and 110).

When the determination part 40 determines that the measured value is normal (step 107), the first storage controller 42 opens the electromagnetic valve 26 so as to discharge the sample water remaining in the storage container 22 (first storage container) to the drain (step 108). The measured value obtained by the measurement is stored in the measured value storing part 48 in association with the determination result by the determination part 40 (step 109).

In a case where the determination part 40 determines that the measured value is abnormal (step 110), the second storage controller 44 checks the availability of the storage container 32 based on the history and the like of the transfer operation from the first storage container 22 to the storage container 32 (second storage container) (step 111), and when there is an empty storage container 32, the second storage controller 44 performs a control such that a portion of or the whole sample water in the storage container 22 is transferred to the storage container 32 (step 112). Also in this case, the measured value obtained by the measurement is stored in the measured value storing part 48 in association with the determination result by the determination part 40 (step 113), and the notification of the determination result to a user is performed (step 114). In a case where there is no empty storage container 32 although the determination part 40 determines that the measured value is abnormal, the second storage controller 44 does not perform the operation of transferring the sample water from the storage container 22 to the storage container 32, and the first storage controller 42 discharges the sample water remaining in the storage container 22 to the drain (step 108).

The above operations are exemplified as an example, and some operations such as the operation of notifying the user of the determination result (step 114) may not be always performed.

The embodiment of the water quality analyzer according to the present invention is recapitulated as follows.

The water quality analyzer according to the embodiment of the present invention includes: a sample reservoir including a first storage container configured to temporarily store sample water supplied from a sample water source, and a discharge mechanism configured to discharge the sample water to an outside of the first storage container; at least one second storage container provided as a container different from the first storage container for storing the sample water; a measurement device including a measurement cell for accommodating sample water, the measurement device being configured to obtain a measured value of a physical quantity related to the sample water accommodated in the measurement cell; a pump configured to suction and discharge a liquid, wherein the pump is fluidly connected to any one of the first storage container, the second storage container, and the measurement cell selectively; a switching device configured to switch fluidly connection of the pump with the first storage container, the second storage container and the measurement cell; a determination part configured to determine whether the measured value is normal or abnormal by comparing the measured value with a preset threshold; a measurement controller configured to transfer the sample water stored in the first storage container to the measurement cell using the pump and to perform measurement of the sample water by controlling an operation of the pump and an operation of the switching device; a first storage controller configured to control an operation of the sample reservoir, wherein the first storage controller is configured, after a portion of the sample water stored in the first storage container is supplied to the measurement cell by the pump, to make the sample water stored in the first storage container to remain in the first storage container until the determination part determines the measured value of the sample water which has supplied to the measurement cell, and wherein the first storage controller is configured to discharge the sample water remaining in the first storage container to the outside of the first storage container in a case where the determination part determines that the measured value obtained by the measurement device is normal; and a second storage controller configured to transfer the sample water remaining in the first storage container to the second storage container in a case where the determination part determines that the measured value obtained by the measurement device is abnormal.

In the first configuration example of the above embodiment, the water quality analyzer further includes the measured value storing part that stores the measured value obtained by the measurement device in association with the determination result as to the measured value by the determination part at least in a case where the determination part determines that the measured value obtained by the measurement device is abnormal. With such a configuration example, the measured value determined to be abnormal can be checked later.

In the first configuration example, the water quality analyzer includes the plurality of second storage containers, and the measured value storing part may store the measured value determined as abnormal by the determination part and the second storage container in which the sample water corresponding to the measured value is stored in association with each other. With such a configurational example, when the sample water of which the measured value is determined to be abnormal is verified later, it is possible to easily determine in which second storage container the sample water is stored.

In the second configurational example of the above embodiment, in a case where there is no empty second storage container at the time when the determination part determines that the measured value is abnormal, the second storage controller is configured not to perform an operation of transferring the sample water remaining in the first storage container to an empty second storage container, and the first storage controller is configured to discharge the sample water remaining in the first storage container to the outside of the first storage container. With such a configurational example, it is possible to prevent the plurality of sample waters whose measured values are determined to be abnormal from being mixed in the second storage container.

In the third configurational example of the embodiment, the sample reservoir includes the stirring mechanism for stirring an inside of the first storage container, and the second storage controller is configured to control the sample reservoir so as to make the stirring mechanism stir the inside of the first storage container before the sample water in the first storage container is transferred to the second storage container. With such a configurational example, the sample water in the first storage container before being transferred to the second storage container is stirred by the stirring mechanism and hence, the concentration of the component in the sample water transferred to the second storage container can be set to the same state as the sample water subjected to the measurement.

The fourth configurational example of the embodiment includes the notification part configured to notify a user that the sample water in the first storage container has been transferred to the second storage container when the sample water in the first storage container has been transferred to the second storage container. With such a configurational example, a user can easily recognize that the sample water indicating the abnormal measured value is stored in the second storage container.

In the fifth configurational example of the embodiment, the measurement controller is configured to control operations of the pump and the switching device so that the sample water stored in the second storage container is transferred finally to the measurement cell and is measured when an instruction to perform measurement of the sample water stored in the second storage container is inputted as a final step. According to such a configurational example, the re-measurement of the sample water stored in the second storage container can be performed when the user desires.

DESCRIPTION OF REFERENCE SIGNS

2: Syringe pump (pump)
4, 6: Multi-port valve
8: Reactor
9: Ultraviolet lamp
10: Measurement device
12: Measurement cell
14: Light source
16: Light detection element
18: Pump
20: Sample reservoir
22: Storage container (first storage container)
24: Switching mechanism
26: Electromagnetic valve
28: Stirring mechanism
30: Motor
32: Storage container (second storage container)
34: Flow path selection valve
36: Arithmetic control device
38: Measurement controller
40: Determination part
42: First storage controller
44: Second storage controller
46: Notification part
48: Measured value storing part

The invention claimed is:

1. A water quality analyzer comprising:
a sample reservoir including a first storage container configured to temporarily store sample water supplied from a sample water source, and a discharge mechanism configured to discharge the sample water to an outside of the first storage container;
at least one second storage container provided as a container different from the first storage container for storing the sample water;
a measurement device including a measurement cell for accommodating sample water, the measurement device being configured to obtain a measured value of a physical quantity related to the sample water accommodated in the measurement cell;
a pump configured to suction and discharge a liquid, wherein the pump is selectively and fluidly connected to the first storage container in a first state, the second storage container in a second state, and the measurement cell in a third state via a switching device;
wherein the switching device is configured to switch fluidly connection of the pump with the first storage container, the second storage container and the measurement cell;
a determination part configured to determine whether the measured value is normal or abnormal by comparing the measured value with a preset threshold;
a measurement controller configured to transfer the sample water stored in the first storage container to the measurement cell using the pump and to perform measurement of the sample water by controlling an operation of the pump and an operation of the switching device;
a first storage controller configured to control an operation of the sample reservoir,
wherein the first storage controller is configured, after a portion of the sample water stored in the first storage container is supplied to the measurement cell by the pump, to make the sample water stored in the first storage container to remain in the first storage container until the determination part determines the measured value of the sample water which has supplied to the measurement cell, and
wherein the first storage controller is configured to discharge the sample water remaining in the first storage container to the outside of the first storage container in a case where the determination part determines that the measured value obtained by the measurement device is normal; and
a second storage controller configured to transfer the sample water remaining in the first storage container to the second storage container via the switching device in a case where the determination part determines that the measured value obtained by the measurement device is abnormal,
wherein the measurement controller is configured, when an instruction to perform measurement of the sample water stored in the second storage container is inputted to the measurement controller, to control an operation of the pump and an operation of the switching device so that the sample water stored in the second storage container is transferred finally to the measurement cell and is measured.

2. The water quality analyzer according to claim 1, further comprising a measured value storing part that stores a measured value obtained by the measurement device in association with a determination result as to the measured value by the determination part at least in a case where the determination part determines that the measured value obtained by the measurement device is abnormal.

3. The water quality analyzer according to claim 2, wherein
the water quality analyzer includes a plurality of the second storage containers, and
the measured value storing part stores the measured value determined as abnormal by the determination part and the second storage container in which the sample water corresponding to the measured value is stored in association with each other.

4. The water quality analyzer according to claim 1, further comprising a notification part configured to notify a user that the sample water in the first storage container has been transferred to the second storage container when the sample water in the first storage container has been transferred to the second storage container.

5. The water quality analyzer according to claim 1, wherein the measurement device includes a light source for irradiating light toward the measurement cell and a light detection element for detecting the intensity of the light irradiated from the light source that passes through the measurement cell.

6. A water quality analyzer comprising:
a sample reservoir including a first storage container configured to temporarily store sample water supplied from a sample water source, and a discharge mechanism configured to discharge the sample water to an outside of the first storage container;
at least one second storage container provided as a container different from the first storage container for storing the sample water;
a measurement device including a measurement cell for accommodating sample water, the measurement device being configured to obtain a measured value of a physical quantity related to the sample water accommodated in the measurement cell;
a pump configured to suction and discharge a liquid, wherein the pump is selectively and fluidly connected to the first storage container in a first state, the second storage container in a second state, and the measurement cell in a third state via a switching device;
wherein the switching device is configured to switch fluidly connection of the pump with the first storage container, the second storage container and the measurement cell;
a determination part configured to determine whether the measured value is normal or abnormal by comparing the measured value with a preset threshold;
a measurement controller configured to transfer the sample water stored in the first storage container to the measurement cell using the pump and to perform measurement of the sample water by controlling an operation of the pump and an operation of the switching device;
a first storage controller configured to control an operation of the sample reservoir,
wherein the first storage controller is configured, after a portion of the sample water stored in the first storage container is supplied to the measurement cell by the pump, to make the sample water stored in the first storage container to remain in the first storage container until the determination part determines the measured value of the sample water which has supplied to the measurement cell, and
wherein the first storage controller is configured to discharge the sample water remaining in the first storage container to the outside of the first storage container in a case where the determination part determines that the measured value obtained by the measurement device is normal; and
a second storage controller configured to transfer the sample water remaining in the first storage container to the second storage container via the switching device in a case where the determination part determines that the measured value obtained by the measurement device is abnormal,
wherein, in a case where there is no empty second storage container at the time when the determination part determines that the measured value is abnormal, the second storage controller is configured not to perform an operation of transferring the sample water remaining in the first storage container to an empty second storage container, and the first storage controller is configured to discharge the sample water remaining in the first storage container to the outside of the first storage container.

7. A water quality analyzer comprising:
a sample reservoir including a first storage container configured to temporarily store sample water supplied from a sample water source, and a discharge mechanism configured to discharge the sample water to an outside of the first storage container;
at least one second storage container provided as a container different from the first storage container for storing the sample water;
a measurement device including a measurement cell for accommodating sample water, the measurement device being configured to obtain a measured value of a physical quantity related to the sample water accommodated in the measurement cell;
a pump configured to suction and discharge a liquid, wherein the pump is selectively and fluidly connected to the first storage container in a first state, the second storage container in a second state, and the measurement cell in a third state via a switching device;
wherein the switching device is configured to switch fluidly connection of the pump with the first storage container, the second storage container and the measurement cell;
a determination part configured to determine whether the measured value is normal or abnormal by comparing the measured value with a preset threshold;
a measurement controller configured to transfer the sample water stored in the first storage container to the measurement cell using the pump and to perform measurement of the sample water by controlling an operation of the pump and an operation of the switching device;
a first storage controller configured to control an operation of the sample reservoir,
wherein the first storage controller is configured, after a portion of the sample water stored in the first storage container is supplied to the measurement cell by the pump, to make the sample water stored in the first storage container to remain in the first storage container until the determination part determines the measured value of the sample water which has supplied to the measurement cell, and wherein the first storage controller is configured to discharge the sample water remaining in the first storage container to the outside of the first storage container in a case where the determination part determines that the measured value obtained by the measurement device is normal; and a second storage controller configured to transfer the sample water remaining in the first storage container to the second storage container via the switching device in a case where the determination part determines that the measured value obtained by the measurement device is abnormal, wherein the sample reservoir includes a stirring mechanism for stirring an inside of the first storage container, and the second storage controller is configured to control the sample reservoir so as to make the stirring mechanism stir the inside of the first storage container before the sample water in the first storage container is transferred to the second storage container.

* * * * *